(12) United States Patent
Cunningham (10) Patent No.: US 11,204,399 B2
(45) Date of Patent: Dec. 21, 2021

(54) SYSTEM AND METHOD FOR DEVICE TRACKING VIA MAGNETIC RESONANCE IMAGING WITH LIGHT-MODULATED MAGNETIC SUSCEPTIBILITY MARKERS

(71) Applicant: Sunnybrook Research Institute, Toronto (CA)

(72) Inventor: Charles Cunningham, Toronto (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 793 days.

(21) Appl. No.: 15/526,390

(22) PCT Filed: Nov. 12, 2015

(86) PCT No.: PCT/CA2015/051173
§ 371 (c)(1),
(2) Date: May 12, 2017

(87) PCT Pub. No.: WO2016/074085
PCT Pub. Date: May 19, 2016

(65) Prior Publication Data
US 2017/0336483 A1  Nov. 23, 2017

Related U.S. Application Data

(60) Provisional application No. 62/078,794, filed on Nov. 12, 2014.

(51) Int. Cl.
*G01R 33/28* (2006.01)
*A61B 5/055* (2006.01)
(Continued)

(52) U.S. Cl.
CPC .......... *G01R 33/286* (2013.01); *A61B 5/055* (2013.01); *A61B 5/065* (2013.01);
(Continued)

(58) Field of Classification Search
CPC ..... G01R 33/16; A61B 1/00–32; A61B 17/29; A61B 17/0469; A61B 17/3478; A61B 17/12013; A61B 17/320016
(Continued)

(56) References Cited

U.S. PATENT DOCUMENTS 5,728,079 A  3/1998  Weber
6,236,205 B1 *  5/2001  Ludeke .................. A61B 5/06
324/300
(Continued)

FOREIGN PATENT DOCUMENTS

CA  2833620 A1  10/2012

OTHER PUBLICATIONS

Roth et al., "Temperature Dependence of Laser-Induced Demagnetization in Ni: A Key for Identifying the Underlying Mechanism", American Physical Society, 2, 021006 (2012), pp. 1-7 (Year: 2012).*
(Continued)

*Primary Examiner* — James M Kish
(74) *Attorney, Agent, or Firm* — Quarles & Brady LLP (57) ABSTRACT

Described here are systems and methods for using a laser-induced demagnetization of magnetic particles disbursed in a tracking marker to generate variable susceptibility effects that can be imaged with magnetic resonance imaging ("MRI"). As one example, laser power is delivered to nickel particles using fiber optics. This demagnetization effect can be used in rapid tracking of interventional devices by subtracting the two images acquired when the laser is off and on.

20 Claims, 7 Drawing Sheets

(51) Int. Cl.

| | |
|---|---|
| *A61B 5/06* | (2006.01) |
| *G01R 33/56* | (2006.01) |
| *A61B 5/00* | (2006.01) |
| *A61B 90/30* | (2016.01) |
| *A61B 90/00* | (2016.01) |

(52) U.S. Cl.
CPC ........ *G01R 33/5608* (2013.01); *A61B 5/7292* (2013.01); *A61B 2090/306* (2016.02); *A61B 2090/3954* (2016.02)

(58) Field of Classification Search
USPC .......................................................... 600/424
See application file for complete search history.

(56) References Cited

U.S. PATENT DOCUMENTS

| | | | | |
|---|---|---|---|---|
| 6,430,129 | B1 | 8/2002 | Ohara | |
| 7,742,799 | B2* | 6/2010 | Mueller | A61B 5/055 |
| | | | | 324/304 |
| 8,620,406 | B2* | 12/2013 | Smith | A61M 25/0043 |
| | | | | 600/420 |
| 8,676,295 | B2* | 3/2014 | Cunningham | A61B 5/055 |
| | | | | 600/411 |
| 2003/0073898 | A1* | 4/2003 | Weiss | A61B 5/06 |
| | | | | 600/410 |
| 2005/0043611 | A1* | 2/2005 | Sabo | A61B 5/055 |
| | | | | 600/411 |
| 2006/0106303 | A1* | 5/2006 | Karmarkar | A61M 25/00 |
| | | | | 600/422 |
| 2006/0258934 | A1* | 11/2006 | Zenge | G01R 33/286 |
| | | | | 600/410 |
| 2007/0043288 | A1* | 2/2007 | Mueller | A61B 5/055 |
| | | | | 600/411 |
| 2010/0063383 | A1* | 3/2010 | Anderson | A61M 25/01 |
| | | | | 600/411 |
| 2010/0168553 | A1* | 7/2010 | Martel | A61B 90/36 |
| | | | | 600/411 |
| 2012/0310080 | A1* | 12/2012 | Cunningham | A61B 5/055 |
| | | | | 600/423 |
| 2013/0289533 | A1* | 10/2013 | Duering | A61L 29/126 |
| | | | | 604/529 |
| 2015/0196369 | A1* | 7/2015 | Glossop | G01R 33/287 |
| | | | | 600/409 |

OTHER PUBLICATIONS

Konings et al., "Development of an MR-Safe Tracking Catheter With a Laser-Driven Tip Coil", Journal of Magnetic Resonance Imaging 13 (2001), pp. 131-135. (Year: 2001).*

Beaurepaire E, et al. Ultrafast spin dynamics in ferromagnetic nickel. Phys Rev Lett 1996;76(22):4250-4253.

Dharmakumar R, et al. Generating positive contrast from o?-resonant spins with steady-state free precession magnetic resonance imaging: theory and proof-of-principle experiments. Phys Med Biol 2006;51(17):4201-4215.

Dominguez-Viqueira W, et al. Tracking a 6F Catheter Under MRI Using a Controllable Susceptibility Device: A New Tracking Mechanis. In Proc. 22nd Int. Soc. Magn. Reson. Med. Proc. Int. Soc. Magn. Reson. Med., 2014.

Dominguez-Viqueira, W., et al. "A controllable susceptibility marker for passive device tracking." Magnetic resonance in medicine 72.1 (2014): 269-275.

Dominguez-Viqueira, W. et al. "Passive catheter tracking with a controllable susceptibility effect." Journal of Cardiovascular Magnetic Resonance 15.1 (2013): p. 17.

Draper JN, et al. Passive catheter visualization in magnetic resonance-guided endovascular therapy using multicycle projection dephasers. J Magn Reson Imag-ing 2006;24(1):160-167.

European Patent Office, Extended European Search Report for application 15858645.3, dated Jun. 8, 2018.

Evans DF. A new type of magnetic balance. Journal of Physics E: Scientific Instruments 1974;7(4):247.

Felfoul O, et al. In vivo MR-tracking based on magnetic signature selective excitation. IEEE Trans Med Imaging 2008;27(1):28-35.

International Searching Authority, International Search Report and Written Opinion for application PCT/CA2015/051173, dated Feb. 11, 2016.

Japanese Patent Office, Office Action for application 2017-525566, dated Aug. 27, 2019. With associate translation.

Koopmans B, et al. Explaining the paradoxical diversity of ultrafast laser-induced demagnetization. Nat Mater 2010;9(3):259-265.

Paley, M., et al. "High magnetic susceptibility coatings for visualisation of optical fibres on a specialised interventional MRI system." European radiology 7.8 (1997): 1341-1342.

Patil S, et al. Automatic slice positioning (ASP) for passive real-time tracking of interventional devices using projection-reconstruction imaging with echo-dephasing (PRIDE). Magn Reson Med 2009;62(4):935-942.

Schenck JF. The role of magnetic susceptibility in magnetic resonance imaging: MRI magnetic compatibility of the first and second kinds. Med Phys 1996;23:815-850.

Seppenwoolde JH, et al. Passive tracking exploiting local signal conservation: the white marker phenomenon. Magn Reson Med 2003;50(4):784-790.

Tokoro, H. et al. "One-shot-laser-pulse-induced demagnetization in rubidium manganese hexacyanoferrate." Applied physics letters 82.8 (2003): 1245-1247.

Zhang K, et al. Tracking of an interventional catheter with a ferromagnetic tip using dual-echo projections. J Magn Reson 2013;234:176-183.

* cited by examiner

SYSTEM AND METHOD FOR DEVICE TRACKING VIA MAGNETIC RESONANCE IMAGING WITH LIGHT-MODULATED MAGNETIC SUSCEPTIBILITY MARKERS

CROSS-REFERENCE TO RELATED APPLICATIONS

This application represents the national stage entry of PCT International Application PCT/CA2015/051173 filed Nov. 12, 2015, which claims the benefit of U.S. Provisional Application 62/078,794 filed Nov. 12, 2014. The contents of this application are hereby incorporated by reference as if set forth in their entirety herein.

BACKGROUND OF THE INVENTION

The field of the invention is systems and methods for magnetic resonance imaging ("MRI"). More particularly, the invention relates to systems and methods for tracking an interventional device that can be actuated to induce variable magnetic susceptibility effects.

The placement of interventional devices, such as guide wires and stents, using MRI guidance is a promising and evolving field with great clinical potential. One particular challenge of this field, however, has been how to develop safe and reliable methods for tracking such devices as they are moved and manipulated within vessels or organs.

One effective method for making devices conspicuous in MRI images is to incorporate a marker or set of markers on the device, where the markers are made of a material with a sufficiently large magnetic susceptibility. Examples of such markers include small beads of ferromagnetic material. Examples of MR-visible interventional instruments of this kind are described in U.S. Pat. Nos. 5,728,079 and 6,430,129.

Magnetic materials have been utilized on the interventional tools such as needles, or catheters, as markers for generating contrast in MR images. These magnetic materials have been used to produce negative or positive contrast in their vicinity compare to surrounding tissues. Differences in volume susceptibility values with their surrounding will cause field inhomogeneities which results in signal losses in their vicinity. Volume susceptibility of ferromagnetic materials is substantially large that even small concentration of these material will create substantial signal losses.

However, the ability to track the device as it is manipulated is only present in tomographic slices containing the device (and the markers). If the particular slice containing the device is not known, it is difficult and time-consuming to find the device using these approaches.

SUMMARY OF THE INVENTION

The present invention overcomes the aforementioned drawbacks by providing a tracking device for tracking a medical device using a magnetic resonance imaging ("MRI") system. The tracking device includes a marker containing a magnetic material, an optical source, and an optical fiber coupling the optical source to the marker. Light generated by the optical source is communicated to the marker via the optical fiber to alter a magnetic susceptibility of the magnetic material in the marker.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for rapid measurement of an interventional device marker location by providing a susceptibility effect that can be pulsed (e.g., temporally modulated), which gives the ability to separate the susceptibility effect of the marker from background signals by digital signal processing (e.g., filtering). This background separation enables projection-mode (e.g., volumetric) coverage of large volumes of tissue, which is important for rapid and robust device position measurement.

More particularly, the systems and methods described here utilize a laser-induced demagnetization phenomenon to generate variable susceptibility effects that can be imaged with MRI. As one example, laser power is delivered to nickel ("Ni") particles using fiber optics. Other examples will be described below. In this example, if the laser is off, the susceptibility effect of the Ni particles is similar to that of normal inside the MRI system's magnetic field. However, if the laser is on, the Ni particles will be demagnetized, which results in reduced susceptibility artifacts. This effect can be used in rapid tracking of devices by subtracting the two images acquired when the laser is off and on.

Certain magnetic materials, such as nickel and cobalt, exhibit magneto-optical effects at room temperature, such as demagnetization after irradiation with a pulsed laser. The optical effects are governed by the penetration depth of the light into the material, and have therefore been mainly studied using thin films of metal that are subjected to a magnetic field and laser light. When a sufficient optical fluence is present in the metal (e.g., 2.5 $mJ/cm^2$) a rapid change in magnetic susceptibility is induced in the metal.

Laser-induced demagnetization of thin films and particles of metal, such as nickel and gadolinium, has been a research topic for read-write processes in computer technology. There are two main types of effect on the metals once they are placed in an external magnetic field and are exposed to a laser pulse. The first effects are the optical effects, in which the laser photons directly interact with the electrons in the metal's electron system and cause a change in magnetization within a picosecond time scale.

The second effects are the thermal effects. If the temperature of any magnetic material is increased, the magnetization of the material in an external magnetic field is reduced. If the temperature is increased to the Curie temperature, a ferromagnetic material will become paramagnetic, typically with sharply reduced magnetization. These thermal effects occur when the absorbed laser photons increases the bulk temperature of the metal, and are maximized when the temperature is raised to the Curie temperature and beyond.

As will be described below in more detail, the systems and methods described here implement this effect for tracking or otherwise following or measuring the position of interventional and surgical devices. Examples of interventional and surgical devices that can be tracked in the manner include needles; catheters; applicators, such as ultrasonic and radio frequency ("RF") applicators; and any other device that may be used in connection with MRI-guided procedures.

Figure 1:
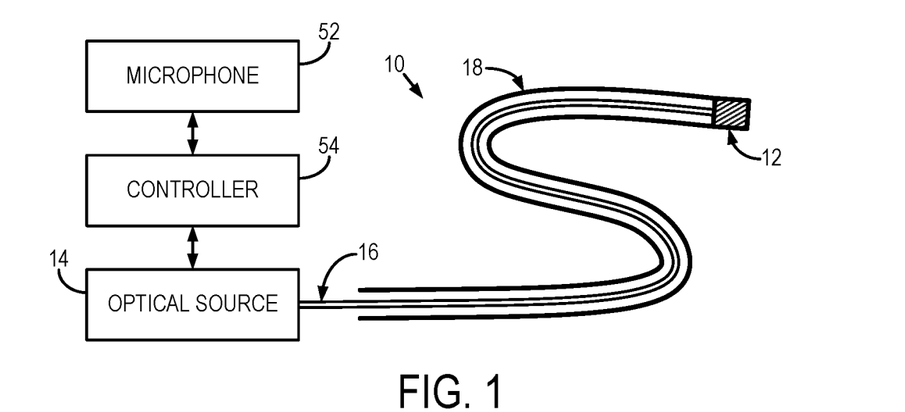
FIG. 1 is a block diagram illustrating an example of a tracking system in accordance with some embodiments of the present invention.

Referring now to FIG. 1, a tracking system 10 generally includes a tracking marker 12 containing a magnetic material. The tracking marker 12 is coupled to an optical source 14 via an optical fiber 16. As described above, the tracking system 10 can be coupled to an interventional device 18, which may include a catheter.

In some embodiments, the optical source 14 includes a laser. As one example, the laser can include a continuous-wave fiber-coupled photodiode laser machine (such as the laser manufactured as model number S1FC808, (Thorlabs Inc.; Newton, N.J., USA) with the maximum power of 24.54 mW. The wavelength of this laser is 808 nm, which is in the near-infrared ("NIR") spectrum.

In one preferred embodiment, the optical source 14 includes a continuous-wave laser having the functionality to temporally modulate the laser output using an analog trigger signal provided by a controller that is synchronized with the MRI data acquisition. As one example, the continuous-wave laser can have 1 W maximum output power and 808 nm wavelength. Having 1 W power output provides sufficient fluence to affect all the magnetic particles within the susceptibility marker, and the temporal modulation of the power reduces the duty cycle of the laser to mitigate any bulk heating of the device.

By way of example, the optical fiber 16 can include a 5 µm fiber optic with 125 µm cladding in a protective Kevlar® layer. In some embodiments, the optical fiber 16 can be coupled to the optical source 14 using a FC/PC connector.

Figure 2:
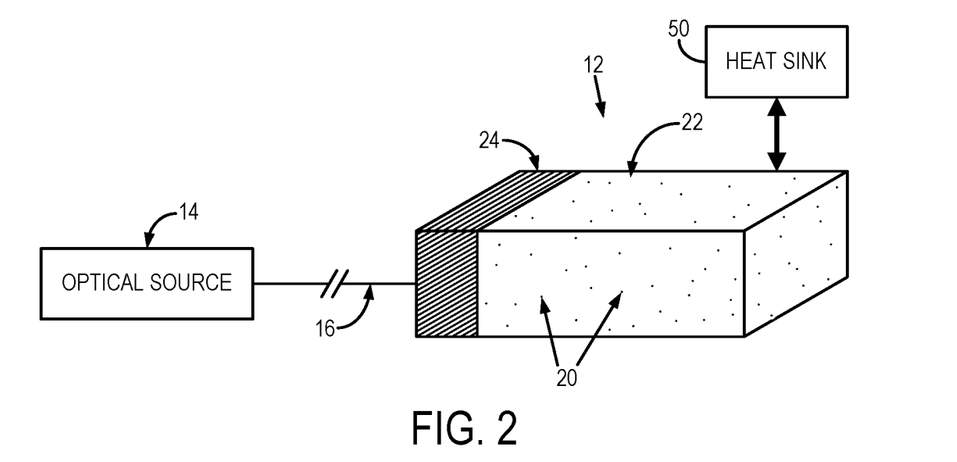
FIG. 2 is a block diagram illustrating an example of a tracking marker that forms a part of the tracking system illustrated in FIG. 1.

Referring now to FIG. 2, an example of the tracking marker 12 is illustrated. In this example, magnetic particles 20 are dispersed throughout a substrate 22 that is coupled to the distal end of the optical fiber 16. In some embodiments, the substrate 22 is a translucent or otherwise transparent material, such as clear or otherwise non-opaque epoxy, a non-opaque plastic, or glass. The magnetic particles 20 can, in some embodiments, include magnetic nanoparticles. As an example, the magnetic particles 20 can be composed of nickel particles, cobalt particles, combinations thereof, or any other suitable magnetic particle or combinations thereof. With the relative volume of magnetic particles 20 in an appropriate range, such as one percent, the magnetic particles 20 and the substrate 22 together will have a sufficiently large magnetic susceptibility to act as a susceptibility marker for tracking, but will still be translucent so that light can reach all of the magnetic particles 20. In some embodiments, the outer surface of the substrate 22 will be coated with a reflective layer, with magnetic susceptibility close to tissue, such as a copper coating, in order to reflect light back towards the magnetic particles 20 and to contain the light within the tracking marker 12.

Figure 3:
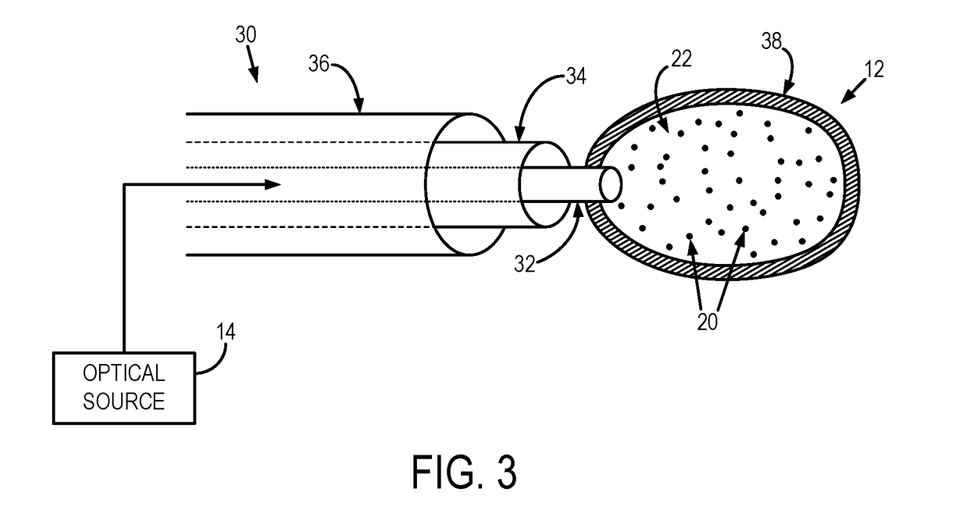
FIG. 3 is a block diagram illustrating another example of a tracking marker that forms a part of a tracking system, such as the tracking system illustrated in FIG. 1.

One specific, and non-limiting example, is illustrated in FIG. 3. In this example, the magnetic particles 20 are dispersed in a substrate 22 composed of glass and coupled to the distal end of an optical fiber 16. The optical fiber 16 is composed of a central optical fiber core 30 surrounded by a fiber cladding 32 and fiber buffer 34. The substrate 22 is coated, at least partially, in a metal layer 36 that reflects light back towards the magnetic particles 20 and to contain the light within the tracking marker 12.

In one preferred embodiment, the change in magnetization of the magnetic particles 20 is maximized by ensuring that all of the magnetic particles 20 are bathed in a sufficient fluence of laser light (as described above). The change in magnetization of the magnetic particles 20 can also be maximized, significantly, by minimizing the susceptibility effects that are not due to the particles affected by the laser light. For example, the reflective coating mentioned above, as well as any other components and coatings used in fabricating the device, can be selected to match the susceptibility of tissue as closely as possible.

As one example, the distal end of the optical fiber 16 can be stripped to expose the cladding layer. Nickel nanopowder particles with an average size smaller than 100 nm (such as those manufactured by Sigma-Aldrich Co.; St Louis, Mo., USA) can be dispersed in the substrate 22.

In some embodiments, the proximal end of the tracking marker 12 can include a diffuser 24 that is coupled on its distal end to the substrate 22 and on its proximal end to the optical fiber 16. The diffuser 24 can include any suitable diffuser for spreading out or otherwise scattering light incident from the optical fiber 16 into the substrate 22. As one example, the diffuser 24 may be composed of a polymer.

Figure 4:
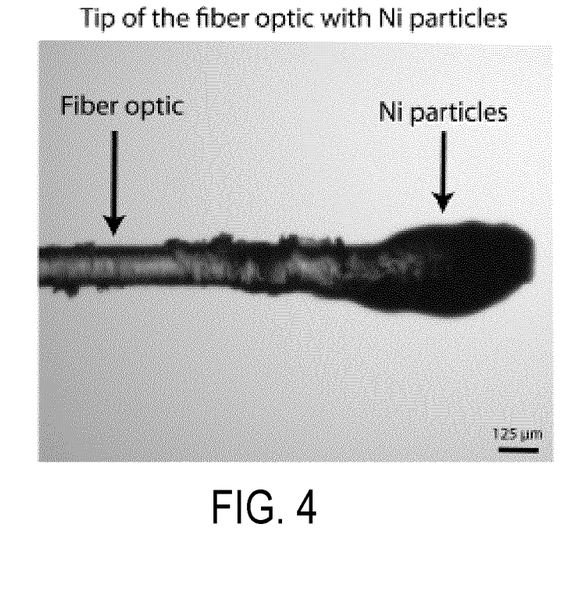
FIG. 4 is a microscopic image of an example tracking marker constructed by coupling nickel particles to the tip of a fiber optic.

In some embodiments, the substrate 22 can simply include a glue, such as a cyanoacrylate glue manufactured by Loctite (Westlake, Ohio, USA). FIG. 4 shows a microscopic image of a tracking marker 12 constructed in this manner.

Figure 5:
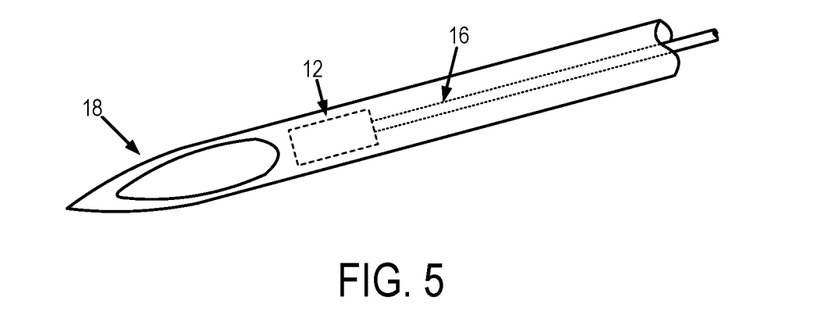
FIG. 5 is an example of a tracking marker incorporated into a biopsy or other medical needle.

In some other embodiments, such as those illustrated in FIG. 1, the substrate 22 containing the particles 20 is machined, molded, or 3D-printed from a suitable optically translucent or transparent material into a small hollow cylinder that can be incorporated into a catheter with a lumen. As illustrated in FIG. 5, in some other embodiments, the substrate 22 containing the particles 20 is molded into a small tracking marker 12, which may be rectangular in shape or may be shaped in other geometries, that can be incorporated into a biopsy needle 24. In some embodiments, the substrate 22 material is selected based on its thermal conductivity, thermal coupling to the magnetic particles 20, specific heat capacity, or combinations thereof. For instance, the substrate 22 material can be selected based on these parameters such that thermal energy deposited in the magnetic particles 20 is adequately dissipated in the substrate 22 and such that the bulk temperature increase in the tracking marker 12 is minimized.

In some other embodiments, a heat sink structure 50 can be incorporated into the structure surrounding the tracking marker 12 in order to mitigate any bulk heating of the device due to absorption of the laser light and to shorten the time required for the magnetic particles 20 to cool and re-magnetize, so that the duration of the pulsing of the magnetic effect of the marker 12 on and off can be sufficiently short. Thus, a heat sink 50 can be thermally coupled to the tracking marker 12 to provide cooling of the tracking marker 12, which reduces the cooling time constant of the tracking marker 12 and, in turn, allows for more rapid modulation of the magnetization state of the magnetic material in the tracking marker 12.

Figure 6:
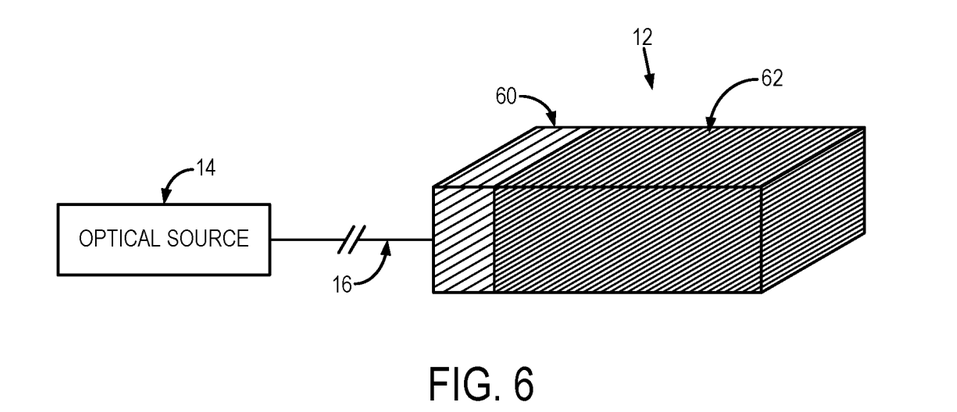
FIG. 6 is an example of a tracking marker that includes a thermal coupling that is heated in response to light from an optical source and transfers this heat to the magnetic material in the tracking marker.

In still other embodiments, such as the one illustrated in FIG. 6, the tracking system 10 can include a thermal coupling 60 positioned between the optical source 14 and the tracking marker 12. The thermal coupling 60 is coupled to the optical source 14 and is thermally coupled to the tracking marker 12. The thermal coupling 60 receives light from optical source 14, which increases the thermal energy of the thermal coupling 60. When the temperature of the thermal coupling 60 is raised, the heat is transferred to the magnetic material 62 in the tracking marker 12, thereby raising the temperature of the magnetic material 62. As described above, by heating the magnetic material 62 its magnetization is reduced, which provides a change in magnetic susceptibility that can be imaged with magnetic resonance imaging. As described above, the magnetic material 62 can include a substrate in which magnetic particles are distributed, but can also include a piece of magnetic material, such as a metal. The thermal coupling 60 can include, for example, a layer of thermally conductive material.

When the tracking marker 12 is exposed to laser light delivered through the optical fiber 16, a demagnetization of the magnetic particles 20 in the tracking maker 12 is induced by thermal effects, non-thermal effects, or both, so that the susceptibility effects of the magnetic particles 20 in the tracking marker 12 are transiently reduced in MR images.

Figure 7:
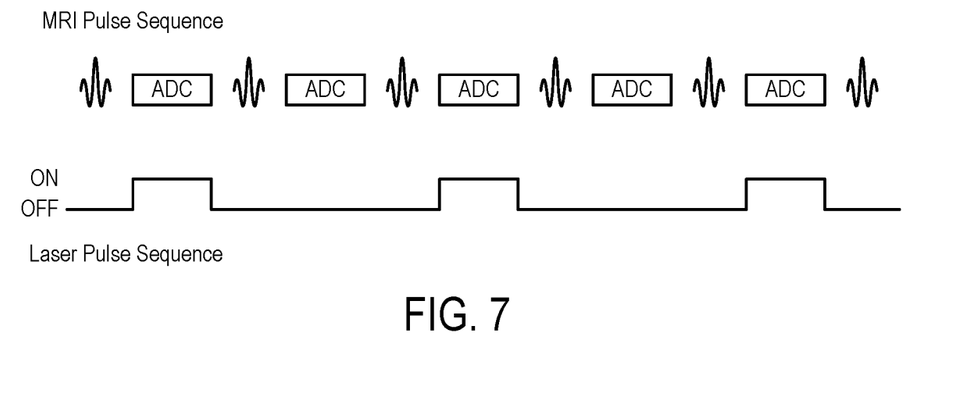
FIG. 7 is an example of a pulse sequence acquisition synchronized with laser pulses.

In some embodiments, the pulses of laser light are applied with sufficient duration (e.g., 5 milliseconds) to affect the magnetic susceptibility of the tracking marker 12 for the duration of an MRI data acquisition window (see FIG. 7).

In some other embodiments, the pulses of laser light are applied in a periodic manner (e.g., every 50 milliseconds) so that a distinctive effect is caused in MRI images. As one example, the distinctive effect can include ghost artifacts. These ghost artifacts will appear at specific spatial offsets from the true location of the device. These spatial offsets can be calculated exactly based on the ratio of the period of the laser pulses and the repetition time ("TR") of the MRI data acquisition pulse sequence. For example, if the period of the laser pulses is chosen such that the light is on for every other data acquisition, as in FIG. 7, then the ghost artifact will appear at an offset of FOV/2 (where FOV is the field-of-view) from the actual location of the device. In one preferred embodiment, the laser light is only turned on during the data acquisition (or every other data acquisition as mentioned above) so that the duty cycle of the laser pulses is kept as low as possible, thereby minimizing heating of the marker.

In one preferred embodiment, the synchronization of the laser pulses with the pulse sequence is accomplished by incorporating a small microphone 52 and controller 54 in the actuator for the optical source 14. The controller 54 may include, for example, a microcontroller. The microphone 52 records the distinct noise emitted by the gradient coils in the MRI system, which can provide the trigger signal for turning the optical source on or off. For instance, the microphone 52 can detect when the gradient coils are operating, and the signals provided by the microphone to the controller 54 can be processed to generate a control signal for the optical source 14 such that the optical source 14 is operated in synchrony with the gradient coils.

In another embodiment, the timing of the laser pulses and the repetitions of the pulse sequence are asynchronous, but with both having a stable frequency, so that a pre-calibration procedure can be used to determine the location of the resulting ghost artifact in magnetic resonance images with the chosen TR. The advantage of this particular embodiment is that no synchronization signal is needed and the design of the actuator for the laser 14 is simpler.

In some other embodiments, it is useful to rapidly locate the position of the device based on projection images. This can be accomplished by making the FOV sufficiently large that the ghost artifact is outside the body or object being imaged. Projection images can be acquired in axial, sagittal, or coronal orientations. In some embodiments, it is useful that the measurement of the location of the ghost artifacts is performed automatically by the operator workstation of the MRI system. In yet another embodiment, the automatically located device position is used to update the slice position of a slice-selective scan, which is automatically started after the device position has been calculated. In another embodiment, the process of creating the ghost artifact in one or more projection images, automatically computing the device location, updating the slice position, and starting a slice-selective scan is initiated by pressing a button on the scan room interface of the MRI system.

One preferred MRI acquisition protocol that can be used to measure and track the position of the tracking marker is now described. Imaging can be performed using a conventional MRI system, such as the one described below. A balanced steady-state-free-precession ("bSSFP") sequence with the following parameters can be used to continuously acquire MR images in rapid succession: TR=5 seconds, TE=2.5 seconds, matrix=256×256, flip angle=60 degrees, slice thickness=300 mm (projection through large volume), FOV=40 cm (substantially larger than the body being imaged, to give room for the ghost artifact in the background). The laser light can be toggled on and off every other TR as shown in FIG. 7, creating a ghost artifact at FOV/2 from the true location of the marker. The orientation of the scan plane can be toggled between axial and sagittal orientations to enable computation of all three co-ordinates of the marker. Alternatively, the plane containing the marker can be computed from just one of the orientations. For example, the coronal plane containing the marker can be computed from a single axial projection image showing the ghost artifact of the marker at FOV/2 from the true device location (with the FOV/2 offset in the phase-encode direction). In this example, the ghost artifact position gives the position in both the sagittal and coronal directions, which can be used to automatically display the coronal slice (or sagittal plane) containing the marker. In a preferred embodiment, the console software can also display a dashed line or other appropriate marker on the image display, indicating the last computed sagittal position of the device, to aid the user in quickly visualizing the device.

Another example of an MRI acquisition protocol that can be implemented to track the tracking marker is now described. Imaging can be performed using a conventional MRI system, such as a 1.5 T scanner. A multiphase fast gradient-recalled echo (Fast GRE) sequence with following parameters can be used to sequentially acquire a series of 36 MR images: matrix size=128×128, flip angle=40, bandwidth=31.3 kHz, FOV=13 cm, slice thickness=5 mm, TR/TE=5.6/2.6 ms, 5 second delay between images, and NEX=1, 10.

Figure 8:
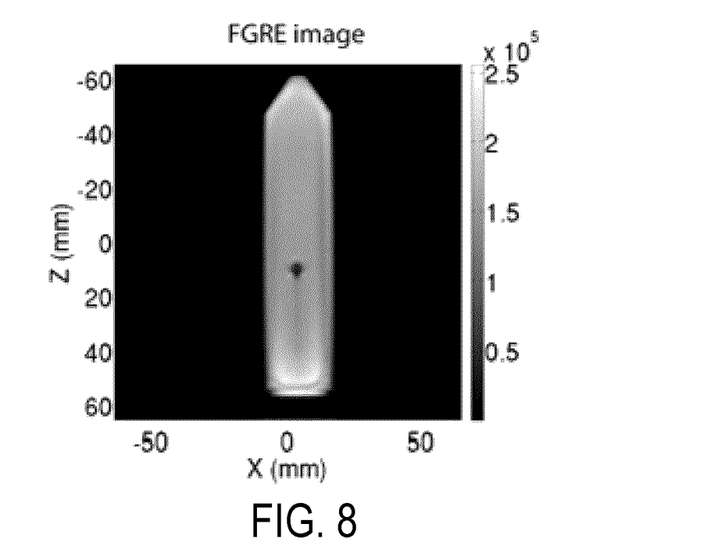
FIG. 8 is an example magnetic resonance image depicting an example tracking marker.

FIG. 8 shows an example of FGRE images with susceptibility artifacts of Ni particles. The laser output power was changed with a trend shown in FIGS. 9A-9B. The same imaging protocol was repeated when the laser was off throughout acquisition of all 36 images.

Complex signal of each voxel through the acquired images can be correlated to the laser output power trend, as follows:

$$CC_{i,j}(0) = \left| \sum_{n=1}^{N} S^*_{i,j}(n+0) L_{i,j}(n) \right|. \quad (1)$$

Eqn. (1) can be used to calculate the cross covariance, and an image can be generated based on the absolute values of $CC_{i,j}$ for each voxel at zero lag between signal of the voxel and laser output power trend. In Eqn. (1), $S^*_{i,j}(n+0)$ is the real signal trend of voxel (i, j) at zero lag and $L_{i,j}(n)$ is the laser output power.

Figure 9A:
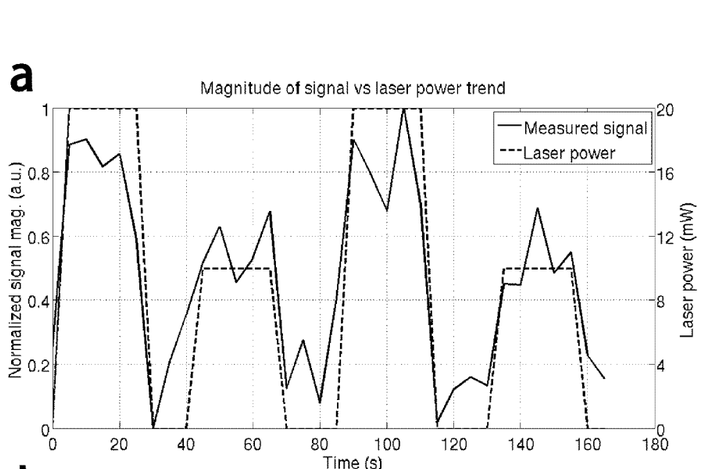
FIGS. 9A-9B illustrate a correlation between laser power output and image signal changes.
Figure 9B:
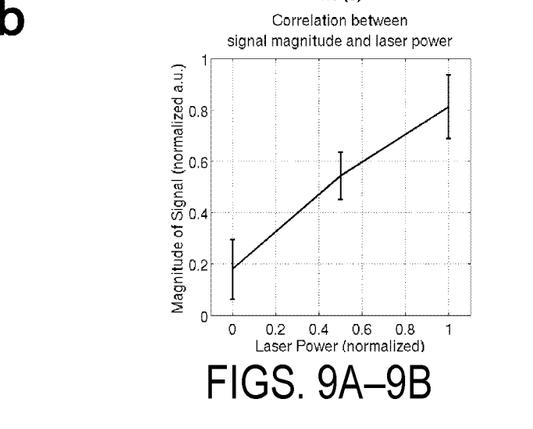

FIGS. 9A-9B also show an example of the magnitude of signal of a voxel that shows high positive correlation with the laser output power. The changes in the signal amplitude is a direct result of the changes in susceptibility value of the nickel particles that are being excited by the laser photons. As a result, the susceptibility artifact changes, thus the magnitude of the voxel signal increases or decreases.

Figure 10A:
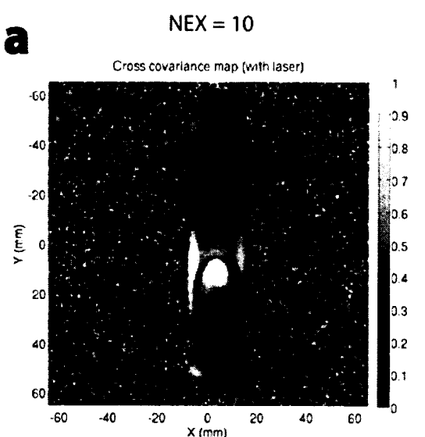
FIGS. 10A-10D depict examples of cross covariance maps of an example tracking marker in both a laser on and a laser off state.
Figure 10B:
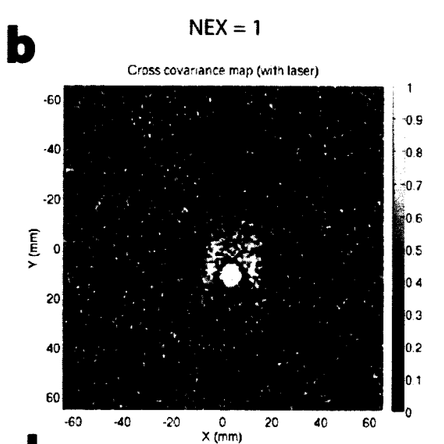
Figure 10C:
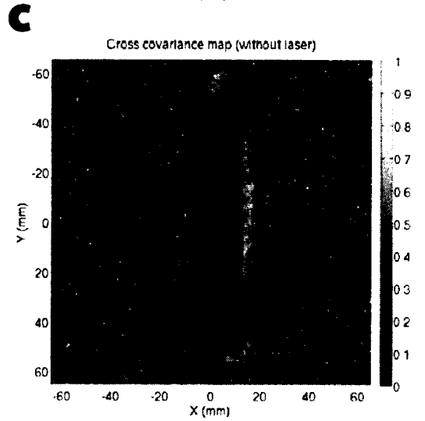
Figure 10D:
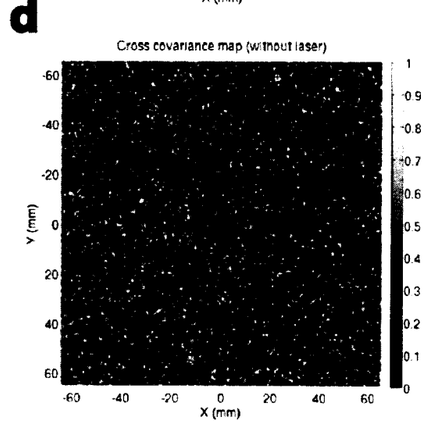

This time-series of images can be analyzed in various ways to compute the position of the marker. Computation of the cross-covariance of the signal time-course of each pixel vs. the time-course of the laser power can be used to detect the device position. FIGS. 10A-10D show examples of cross covariance maps. In particular, FIGS. 10A and 10B show examples of the cross covariance maps for NEX equal to 10 and 1 respectively. The highly correlated voxels were located where there was susceptibility artifact from the nickel particles. FIGS. 10C and 10D illustrate examples of the cross covariance maps for NEX equal to 10 and 1, respectively, in which the laser was off for all acquired images. The results in FIGS. 10C and 10D show that the highly correlated voxels, shown in FIGS. 10A and 10D, were caused by the laser. In some embodiments, the time-course of the laser power can be chosen to augment detection by the cross-covariance or cross-correlation analysis mentioned above. For example, the laser power can be temporally modulated according to a Barker code, such as the Barker-7 code, (1 1 1 0 0 1 0), which will minimize background correlation that interferes with marker detection in low SNR images.

Figures 11A, 11B:
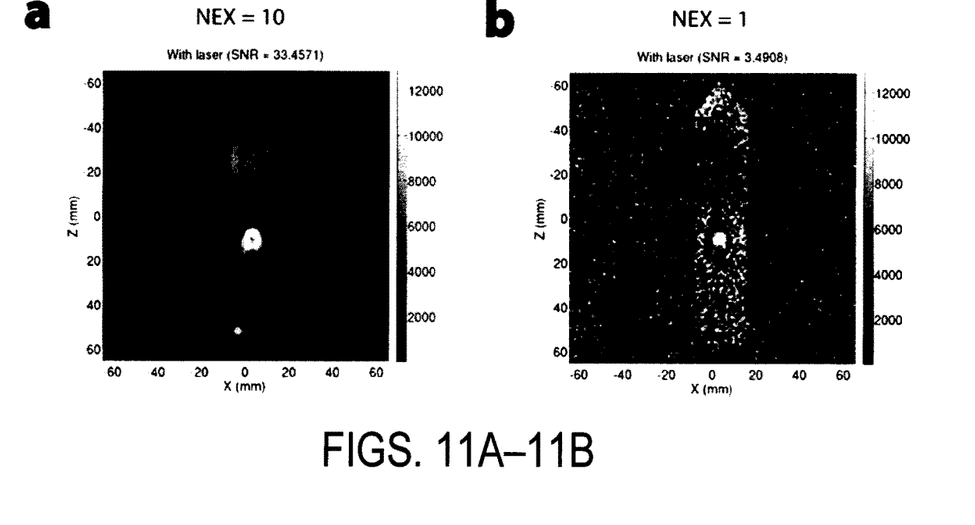
FIGS. 11A-11B depict examples of difference images produced by subtracting images of a tracking marker in a laser-on state and a laser-off state.

In some embodiments, to visualize the changes in susceptibility artifact of the magnetic particles images acquired with the laser on and images acquired with the laser off can be subtracted from each other. FIGS. 11A-11B show examples of the magnitude of subtraction images for NEX equal to 10 and 1, respectively. The subtraction images show differences in signal intensity when the laser was on.

In some embodiments, temporal filtering of sequentially acquired images can be used to visualize the changes in the susceptibility artifact surrounding the marker. For example, spiral-bSSFP images (TR=10 ms, TE=minimum, 128×128 matrix, 100 ms per frame, 2 mm spatial resolution, 10 mm slice thickness) could be acquired sequentially in a continuous fashion, with the laser power toggled on for every third data acquisition (300 ms apart). Temporal filtering of the images with a bandpass at 3.33 Hz can the be used to detect the marker position. In some embodiments, the temporal on-off pattern of the laser pulses can be a code, such as a binary Golay code, with the detection of the device's effect in the resulting images involving the appropriate inverse transformation.

Figure 12:
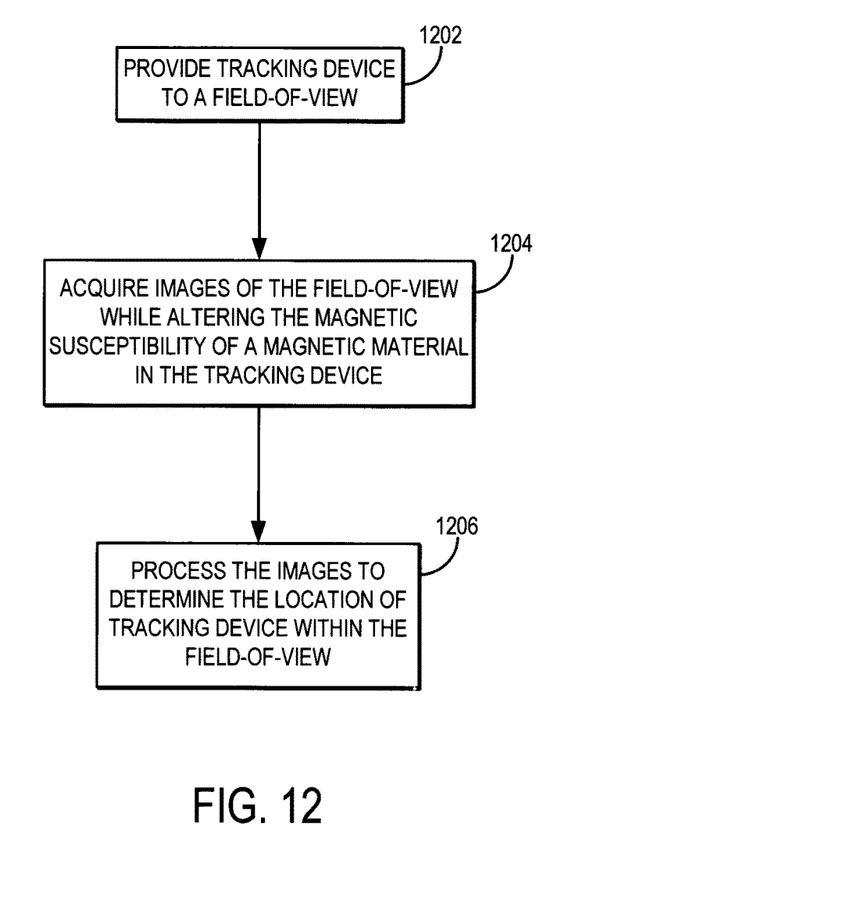
FIG. 12 is a flowchart setting forth the steps of an example method for determining a position of an example tracking marker using MRI.

Referring now to FIG. 12, a flowchart is illustrated as setting forth the steps for an example method for tracking the position of the tracking device described above. The method includes providing the tracking device to a field-of-view, as indicated at step 1202. As one example, this step can include providing the tracking device via an interventional device, such as a catheter, to a region in a subject's body that will be imaged by an MRI system. Images of the field-of-view are then acquired with an MRI system while the magnetic susceptibility of the magnetic material in the tracking device is altered, as indicated at step 1204. For instance, the magnetic susceptibility of the magnetic material in the tracking device is altered according to a temporal pattern of modulation defined by turning the optical source on and off, as described above. As one example, a controller in communication with the optical source provides a control signal that operates the optical source in accordance with the temporal pattern of modulation. The acquired images are then processed to determine the location of the tracking device in the field-of-view, as indicated at step 1206.

As one example, the images are processed to decode the magnetic resonance signals depicted in the images, wherein the decoding of the magnetic resonance signals is performed based on the temporal pattern of modulation. As another example, the images are processed to identify ghost artifacts in the images and to relate the location of the ghost artifacts to the location of the tracking device. In some embodiments, the images can be processed by applying a bandpass filter to the images. In these instances, the bandpass filter is preferably designed to have a center frequency defined by the frequency of the temporal pattern of modulation. Other examples of how the location of the tracking device can be determined from these images are described above.

Thus, systems and methods for laser-induced demagnetization of magnetic particles for passive tracking of a medical device have been described. Experimental results suggested that laser photons interact with magnetic particles, such as nickel particles, through the demagnetization process, thus changing the susceptibility values of the particles. Signals of the voxels around the magnetic particles are highly correlated with the laser output power trend.

Figure 13:
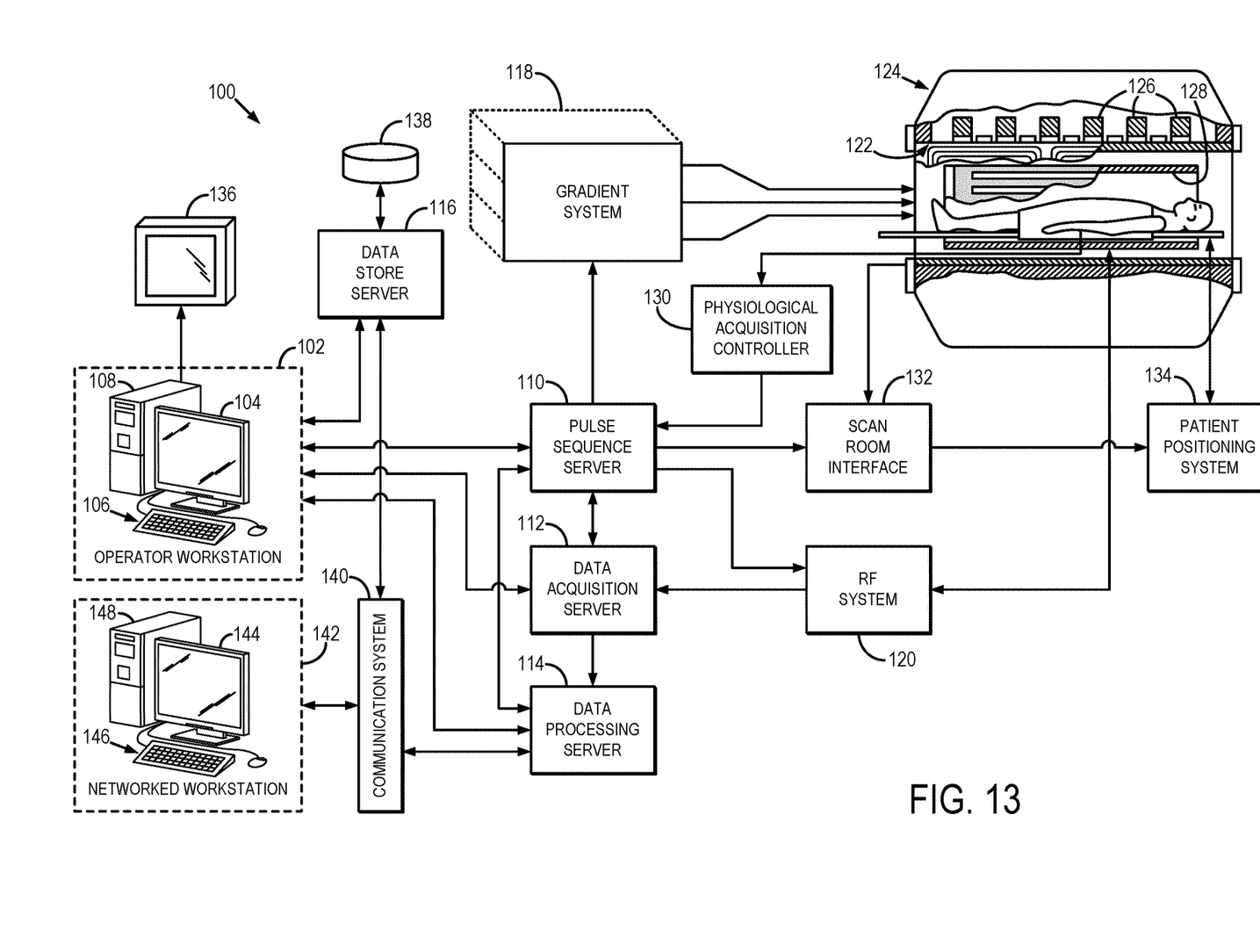
FIG. 13 is a block diagram of an example of an MRI system.

Referring particularly now to FIG. 13, an example of a magnetic resonance imaging ("MRI") system 100 is illustrated. The MRI system 100 includes an operator workstation 102, which will typically include a display 104; one or more input devices 106, such as a keyboard and mouse; and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 13), in order to perform the prescribed magnetic resonance pulse sequence. Responsive magnetic resonance signals detected by the RF coil 128, or a separate local coil (not shown in FIG. 13), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 13).

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad (2);$$

and the phase of the received magnetic resonance signal may also be determined according to the following relationship:

$$\varphi = \tan^{-1}\left(\frac{Q}{I}\right). \qquad (3)$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography ("MRA") scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 13), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

In accordance with the present invention, the operator workstation 102 may include software and hardware components associated with triggering the laser pulses that are synchronized with the pulse sequence, as shown in FIG. 7. For example, the executable code that generates the RF and gradient pulses could be configured to create a TTL pulse that coincides with the start of each readout interval, and this could be connected via a dedicated BNC cable to the laser driver electronics such that the laser power can toggled on and off in synchrony with the beginning and end of the MRI data readout windows.

In addition, the operator workstation 102 may execute software components or plug-ins associated with the processing of the image data acquired during operation of the present tracking system and the automatic update of scan prescription information, such as slice position. These software components can be integral to one or more preferred embodiments of the present invention. For example, the operator workstation may execute a sequence of operations whereby a pulse sequence that is synchronized with the laser pulses is played out, the image data is processed to automatically measure of the location of the ghost artifacts and to derive the device position, and this device position is used to update the slice position of a real-time slice-selective scan, which is automatically started after the device position has been calculated. In one preferred embodiment, this sequence of operations can be initiated by pressing a button on the scan room interface 132, and the resulting slice-selective scan containing the device can be displayed on a MRI-compatible monitor within the scan room.

The present invention has been described in terms of one or more preferred embodiments, and it should be appreciated that many equivalents, alternatives, variations, and modifications, aside from those expressly stated, are possible and within the scope of the invention.

The invention claimed is:

1. A tracking device for tracking a medical device using a magnetic resonance imaging (MRI) system, the tracking system comprising:
   a marker containing a magnetic material, wherein the magnetic material comprises magnetic particles and the marker comprises substrate in which the magnetic particles are distributed;
   an optical source;
   an optical fiber coupling the optical source to the marker;
   wherein light generated by the optical source is communicated to the marker via the optical fiber to alter a magnetic susceptibility of the magnetic material in the maker, and
   the altered magnetic susceptibility of the magnetic material from the light causes the marker to be visible in an MRI image.

2. The tracking device as recited in claim 1, wherein the substrate is composed of an optically translucent material.

3. The tracking device as recited in claim 1, wherein the substrate is composed of an optically transparent material.

4. The tracking device as recited in claim 1, wherein the magnetic particles comprise a plurality of nickel particles.

5. The tracking device as recited in claim 4, wherein the nickel particles are nickel nanoparticles.

6. The tracking device as recited in claim 1, wherein the substrate is composed of at least one of a non-opaque epoxy, a non-opaque plastic, or glass.

7. The tracking device as recited in claim 1, further comprising a diffuser positioned between the optical fiber and the marker, the diffuser being coupled to a distal end of the optical fiber and to a proximal end of the marker.

8. The tracking device as recited in claim 1, wherein the optical source comprises a laser.

9. The tracking device as recited in claim 1, further comprising a thermal coupling positioned between the optical fiber and the marker, wherein light generated by the optical source is communicated to and raises a temperature of the thermal coupling, such that a temperature of the marker is also raised to alter the magnetic susceptibility of the magnetic material in the marker.

10. The tracking device as recited in claim 9, further comprising a heat sink thermally coupled to the marker, wherein the heat sink provides cooling of the marker thereby reducing a cooling time constant of the marker.

11. The tracking device as recited in claim 1, further comprising a controller in communication with the optical source, wherein the controller sends signals to the optical source based on a pulse timing sequence that defines a temporal pattern of modulation according to which the magnetic susceptibility of the magnetic material will be altered.

12. The tracking device of claim 1, wherein the altered magnetic susceptibility of the magnetic marker is caused by a non-thermal effect.

13. A method for determining the location of a tracking device using a magnetic resonance imaging (MM) system including a field-of-view within a bore of the MRI system, the steps of the method comprising:
   (a) providing the marker and optical fiber of the tracking device of claim 11 to the field-of-view;
   (b) acquiring images, via the MRI system, of the field-of-view while altering the magnetic susceptibility of the magnetic material in the device according to the temporal pattern of modulation; and
   (c) processing the images to determine a location of the device within the field-of-view.

14. The method as recited in claim 13, wherein processing the images includes decoding magnetic resonance signals in the images based on the temporal pattern of modulation.

15. The method as recited in claim 13, wherein processing the images includes identifying ghost artifacts in the images resulting from the magnetic susceptibility of the magnetic material being altered according to the temporal pattern of modulation and computing the location of the device in the field-of-view based on a location of the ghost artifacts.

16. The method as recited in claim 13, wherein processing the images includes applying a bandpass filter to the images, wherein the bandpass filter is centered on a frequency of the temporal pattern of modulation.

17. A tracking device for tracking a medical device using a magnetic resonance imaging (MRI) system, the tracking system comprising:
- a marker containing a magnetic material, wherein the magnetic material comprises magnetic particles and the marker comprises a substrate in which the magnetic particles are distributed, wherein the substrate is coated in a metallic layer that reflects light generated by the optical source and communicated to the substrate via the optical fiber back into the substrate;
- an optical source;
- an optical fiber coupling the optical source to the marker;
- wherein light generated by the optical source is communicated to the marker via the optical fiber to alter a magnetic susceptibility of the magnetic material in the marker.

18. The tracking device as recited in claim 17, wherein the substrate is composed of one of an optically translucent material or an optically transparent material.

19. The tracking device as recited in claim 17, wherein the magnetic particles comprise a plurality of nickel particles.

20. The tracking device as recited in claim 19, wherein the nickel particles are nickel nanoparticles.

* * * * *

UNITED STATES PATENT AND TRADEMARK OFFICE
CERTIFICATE OF CORRECTION

| | | |
|---|---|---|
| PATENT NO. | : 11,204,399 B2 | Page 1 of 1 |
| APPLICATION NO. | : 15/526390 | |
| DATED | : December 21, 2021 | |
| INVENTOR(S) | : Charles Cunningham | |

It is certified that error appears in the above-identified patent and that said Letters Patent is hereby corrected as shown below:

In the Claims

Claim 1, Column 11, Line 67: "maker" should be "marker"

Claim 13, Column 12, Line 44: "(MM)" should be "(MRI)"

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*